United States Patent [19]

Endo et al.

[11] Patent Number: 4,883,569

[45] Date of Patent: Nov. 28, 1989

[54] METHOD FOR THE PREPARATION OF A CYCLOALKYL SILANE COMPOUND

[75] Inventors: Mikio Endo; Minoru Takamizawa; Toshinobu Ishihara; Tohru Kubota, all of Niigata; Toshio Shinohara, Gunma, all of Japan

[73] Assignee: Shin-Etsu Chemical Co., Ltd., Tokyo, Japan

[21] Appl. No.: 154,691

[22] Filed: Feb. 11, 1988

[30] Foreign Application Priority Data

Feb. 13, 1987 [JP] Japan ................................. 62-30994

[51] Int. Cl.$^4$ ............................................... B01J 19/2
[52] U.S. Cl. ................................ 204/157.74; 556/449
[58] Field of Search .................... 556/479; 204/157.74, 204/157.61, 157.6

[56] References Cited

U.S. PATENT DOCUMENTS

| | | | |
|---|---|---|---|
| 4,038,302 | 7/1977 | Reichel | 556/479 |
| 4,398,010 | 8/1983 | Adkins | 556/10 |
| 4,450,283 | 5/1984 | McAfee | 556/479 |
| 4,530,879 | 7/1985 | Drabnak | 204/157.74 |
| 4,600,484 | 7/1986 | Drabnak | 204/157.74 |

FOREIGN PATENT DOCUMENTS 49-28189  7/1974  Japan ............................. 204/157.74

*Primary Examiner*—John F. Niebling
*Assistant Examiner*—Ben C. Hsing
*Attorney, Agent, or Firm*—Millen, White & Zelano

[57] ABSTRACT

Cycloalkyl silane compound such as cyclohexyl methyl dichlorosilane can be efficiently prepared by the photochemically induced hydrosilylation reaction. For example, an equimolar mixture of cyclohexene and methyl dichlorosilane with admixture of a catalytic amount of an alcoholic solution of, chloroplatinic acid, is irradiated at a temperature up to 70° C. with ultraviolet light so that the hydrosilylation reaction takes place and proceeds almost to completeness without deactivation of the platinum catalyst to give the desired product in a yield of 90% or even higher.

9 Claims, No Drawings

METHOD FOR THE PREPARATION OF A CYCLOALKYL SILANE COMPOUND

BACKGROUND OF THE INVENTION

The present invention relates to a method for the preparation of a cycloalkyl silane compound or, more particularly, to a method for the preparation of a cycloalkyl silane compound having a saturated cyclic group, which is useful as an intermediate for the synthesis of various kinds of organopolysilanes, organopolysiloxanes and as a silylating agent having stereospecificity, by the hydrosilylation reaction between an unsaturated cyclic hydrocarbon compound such as cyclohexene and a hydrogen silane compound in the presence of a platinum catalyst.

It is well known that a cycloalkyl silane compound having a saturated cyclic hydrocarbon group, such as a cyclohexyl silane compound, can be obtained by the hydrosilylation reaction between an unsaturated cyclic hydrocarbon compound such as cyclohexene and a hydrogen silane compound such as methyl dichlorosilane in the presence of a platinum catalyst. The yield of the desired product is usually low in the above mentioned prior art method and it is generally understood that the yield can be noticeably increased only with extreme difficulties.

To describe a particular prior art method for the preparation of a cycloalkyl silane compound, it has been reported in Journal of the American Chemical Society, volume 79, page 947 (1975) that methyl cyclohexyl dichlorosilane can be obtained almost quantitatively by the reaction of cyclohexene and methyl dichlorosilane in the presence of chloroplatinic acid $H_2PtCl_6 \cdot 6H_2O$ when the mixture is sealed in a glass ampule and heated in boiling water for 20 hours. This result is, however, not reproducible and the result of the subsequently repeated experiments was that the highest yield of the desired reaction product was only about 15% in the reaction mixture and the reaction could proceed no longer even by further continued heating of the mixture. It is also reported in U.S. Pat. No. 3,220,972 that the same cycloalkyl silane compound can be obtained in a yield of 50% by the hydrosilylation reaction of cyclohexene and methyl dichlorosilane in a glass ampule at 100° C. for 6 hours when the reaction is carried out in the presence of an activated platinum catalyst prepared by a heat treatment of a mixture of chloroplatinic acid and n-octyl alcohol followed by removal of hydrogen chloride, water and unreated n-octyl alcohol. This method is also not quite satisfactory because a yield of larger than 50% of the desired product can hardly be obtained due to the deactivation of the platinum catalyst in the course of the reaction.

An attempt has been made and reported in Journal of Organometallic Chemistry, volume 50, page 297 (1973) to perform the above mentioned hydrosilylation reaction in the presence of a nickel complex as the catalyst. This method is industrially not practicable because by-products are necessarily produced in large amounts.

Thus, the only method for the industrial production of a cycloalkyl silane compound having a saturated cyclic hydrocarbon group is the Grignard reaction between a halogen-containing saturated hydrocarbon compound such as chlorocyclohexane and an alkyl halogenosilane such as methyl trichlorosilane. This method by the Grignard reaction is industrially not quite satisfactory in respect of the productivity because the reaction must be performed by diluting the reaction mixture with a large volume of a solvent and a magnesium salt is always produced as a by-product and precipitated in the reaction mixture so that expensive facilities must be provided for the recovery of the solvent and separation of the precipitated magnesium salt leading to an increase in the production cost of the product if not to mention the yield of the desired product which cannot be high enough inherently.

SUMMARY OF THE INVENTION

The present invention accordingly has an object to provide an efficient method for the preparation of a cycloalkyl silane compound having a saturated cyclic hydrocarbon group free from the above described problems and disadvantages in the prior art methods by the hydrosilylation as well as the Grignard method.

Thus, the method of the present invention for the preparation of a cycloalkyl silane compound comprises:

(A) admixing an unsaturated cyclic hydrocarbon compound represented by the general formula

$$C_m R^1{}_n A_p, \qquad (I)$$

in which $R^1$ is a hydrogen atom, a fluorine atom or a flourine-substituted or unsubstituted monovalent hydrocarbon group having 1 to 8 carbon atoms, A is a divalent intramolecular bridging group selected from methylene group $>CH_2$ and dimethylmethylene group $>C(CH_3)_2$, m is an integer of 4 to 8, p is zero or 1 and n is an integer given by $n=2m-2p-2$, with a hydrogen silane compound represented by the general formula

$$HR^2{}_q SiX_{3-q}, \qquad (II)$$

in which $R^2$ is an unsubstituted or substituted monovalent hydrocarbon group, X is a halogen atom or an alkoxy group and q is zero, 1 or 2, and a platinum catalyst to form a reaction mixture; and (B) irradiating the reaction mixture with light or, preferably, ultraviolet light to effect the hydrosilylation reaction between the unsaturated cyclic hydrocarbon compound and the hydrogen silane compound.

DETAILED DESCRIPTION OF THE PREFERRED EMBODIMENTS

The above described method of the present invention is characteristic in the photochemically induced hydrosilylation reaction taking place in a reaction mixture composed of the above defined unsaturated cyclic hydrocarbon compound and hydrogen silane compound with admixture of a catalytic amount of a platinum catalyst. Advantageously and quite unexpectedly, the platinum catalyst under irradiation with light is free from deactivation in the proceeding of the reaction so that the reaction can proceed almost to completion to give the desired cycloalkyl silane compound in a yield of 90% or even higher. For example, the reaction is complete within 10 hours at 70° C. under normal pressure so that the method is industrially advantageous for the preparation of a cycloalkyl silane compound.

One of the reactants in the inventive method is an unsaturated cyclic hydrocarbon compound represented by the above given general formula $C_m R^1{}_n A_p$. In the formula, $R^1$ is a hydrogen atom, a flourine atom or a monovalent hydrocarbon group having 1 to 8 carbon atoms such as alkyl groups, e.g., methyl, ethyl, propyl, butyl and octyl groups, and aryl groups, e.g. phenyl and tolyl groups, optionally, substituted by a fluorine atom or fluorine atoms for a part or all of the hydrogen atoms in the above named hydrocarbon groups. The symbol A in the formula denotes a divalent intramolecular bridging group selected from methylene group $>CH_2$ and dimethylmethylene group $>C(CH_3)_2$. The subscript m is an integer of 4 to 8, p is zero or 1 and n is an integer given by $n=2m-2p-2$.

The unsaturated hydrocarbon compounds in conformity with the general formula (I) and definitions of the symbols therein include cyclohexene $C_6H_{10}$, cycloheptene $C_7H_{12}$, 1-methyl-1-cyclohexene $C_6H_9CH_3$, 4-methyl-1-cyclohexene $C_6H_9CH_3$, norbornylene, 5-perfluorohexyl norbornylene, bornylene and the like. The unsaturated cyclic hydrocarbon compound as the reactant in the inventive method should of course be selected from the above named compounds according to the desired product.

The other reactant to be reacted with the above described unsaturated cyclic hydrocarbon compounds is a hydrogen silane compound represented by the general formula $HR^2_qSiX_{3-q}$. In the formula, $R^2$ is a monovalent hydrocarbon group such as alkyl groups, e.g., methyl, ethyl, propyl and butyl groups, and aryl groups, e.g., phenyl and tolyl groups, as well as those substituted groups obtained by replacing a part or all of the hydrogen atoms in the above named hydrocarbon groups with substituents such as halogen atoms, cyano group and the like, e.g., chloromethyl, 3,3,3-trifluoropropyl and 2-cyanoethyl groups. The symbol X in the formula denotes an atom of halogen, e.g., chlorine, bromine and iodine, or an alkoxy group, e.g., methoxy, ethoxy, propoxy and butoxy groups. The subscript q is zero, 1 or 2. Suitable hydrogen silane compounds include trichlorosilane, methyl dichlorosilane, dimethyl chlorosilane, trimethoxy silane, methyl diethoxy silane and the like.

The platinum compound used as the catalyst for the hydrosilylation reaction may be any of known platinum compounds used conventionally in the hydrosilylation reaction but it is preferably chloroplatinic acid which is used either as such or in the form of a solution in an alcoholic solvent or a complex compound with an olefin or vinyl siloxane. The amount of the platinum compound added to the reaction mixture is not particularly limitative provided that a substantial promoting effect can be obtained on the velocity of the hydrosilylation. The amount should usually be at least 20 ppm or, preferably, at least 40 ppm by weight calculated as platinum based on the amount of the hydrogen silane compound.

The method of the invention is performed by irradiating the reaction mixture prepared by mixing the above described unsaturated cyclic hydrocarbon compound, hydrogen silane compound and platinum compound with light to effect the hydrosilylation reaction. The nature of the light is not particularly limitative and the reaction can proceed, for example, by exposing the reaction mixture to sun light. It is industrially preferable, however, that the light is ultraviolet light emitted from a suitable ultraviolet lamp such as low-pressure and high-pressure mercury lamps.

The hydrosilylation reaction of the inventive method is performed by introducing the unsaturated cyclic hydrocarbon compound and the hydrogen silane compound together with a platinum compound into a reaction vessel having a window for ultraviolet irradiation and equipped with a reflux condenser and a stirrer equipment and irradiating the reaction mixture in the vessel with ultraviolet light through the window. The amounts of the unsaturated cyclic hydrocarbon compound and the hydrogen silane compound should usually be equimolar but it is optional to increase the amount of either one of the reactants over equimolar according to need. It is advantageous from the standpoint of safety that the unsaturated cyclic hydrocarbon compound and the platinum compound are first introduced into the reaction vessel and the hydrogen silane compound is added dropwise into the mixture in the vessel under agitation because the hydrogen silane compound itself is subject to a disproportionation reaction under the reaction conditions.

Although the hydrosilylation reaction of the inventive method can proceed at room temperature, the reaction mixture may be heated at 60° to 70° C. when acceleration of the reaction is desired. An excessively high temperature of, for example, 80° C. or higher is undesirable because the reaction velocity is rather decreased at such a high temperature. The reaction mixture to be irradiated with ultraviolet light is prepared usually without using any solvent but it is optional to dilute the reaction mixture with a suitable inert organic solvent such as octane, toluene, xylene and the like according to need.

In the following, the method of the invention is described in more detail by way of examples and comparative examples.

EXAMPLE 1 AND COMPARATIVE EXAMPLE 1

Cyclohexene and methyl dichlorsilane each in an amount of 1.0 mole were introduced into a glass-made reaction vessel of 250 ml capacity equipped with a reflux condenser and stirrer equipment and having a window for irradiation with light together with 0.43 g of a platinum catalyst, which had been prepared by heating chloroplatinic acid in 2-ethylhexyl alcohol followed by removal of hydrogen chloride, water and unreacted 2-ethylhexyl alcohol, containing 2% by weight of platinum, to form a reaction mixture. The amount of the platinum catalyst corresponded to 200 ppm by weight calculated as $H_2PtCl_6.6H_2O$ based on the amount of methyl dichlorosilane.

The thus prepared reaction mixture was irradiated at 20° C. with ultraviolet light emitted from a high-pressure mercury lamp (Model UN-102, manufactured by Ushio Electric Co.) so that the hydrosilylation reaction between the reactants took place and proceeded exothermically to increase the temperature of the reaction mixture by 5° to 6° C. above the starting temperature until the reaction came near the completion after 40 hours of the ultraviolet irradiation. Thereafter, the reaction mixture was subjected to distillation to give the desired cyclohexyl methyl dichlorosilane in a yield of about 90%.

For comparison, an attempt was made to perform the hydrosilylation reaction in the same reaction mixture as above by heating the reaction mixture under reflux without irradiation with ultraviolet light. The temperature of the reaction mixture was 55° C. at the start of the reaction and gradually increased up to 71° C. after 20 hours to level off. Analysis of the thus obtained reaction mixture indicated that the yield of the desired cyclohexyl methyl dichlorosilane was only 9%. No improvement could be obtained in the yield of the product by further continued heating of the reaction mixture.

For further comparison, the hydrosilylation reaction of the same reaction mixture as above excepting increase of the amount of the platinum catalyst to 1.08 g corresponding to 500 ppm as $H_2PtCl_6.6H_2O$ based on the amount of methyl dichlorosilane was performed in a stainless steel-made autoclave equipped with a stirrer by heating the reaction mixture at 100° C. The yield of 5 cyclohexyl methyl dichlorosilane was 32% after 7 hours of reaction and increased to 34% nearly to level off accordinng to the results of the gas chromatographic analysis. Distillation of the reaction mixture gave the desired product in a yield of only 30% based on the theoretical value.

EXAMPLE 2

Into the same reaction vessel as used in Example 1 was introduced 1.0 mole of cyclohexene admixed with 0.21 g of the same platinum catalyst as used in Example 1 and the mixture in the vessel was heated at 70° C. Thereafter, 0.5 mole of methyl dichlorosilane was added dropwise to the mixture in the reaction vessel to find almost no indication of the proceeding reaction insofar as the reaction vessel was kept in dark.

The reaction mixture in the vessel was then irradiated with ultraviolet light emitted from a high-pressure mercury lamp to find the reaction taking place. Methyl dichlorosilane was further added to the reaction mixture dropwise in an additional amount of 0.7 mole and the reaction was continued under irradiation with ultraviolet light until the reaction was nearly completed after 8 hours. Distillation of the thus obtained reaction mixture after completion of the reaction gave the desired cyclohexyl methyl dichlorosilane in a yield of 95%.

EXAMPLE 3

Into the same reaction vessel as used in Example 1 was introduced 1.0 mole of cyclohexene with admixture of 0.18 g of the same platinum catalyst as used in Example 1 and the mixture in the vessel was heated at 70° C. Thereafter, 1.0 mole of methyl dichlorosilane was added dropwise into the reaction mixture in the vessel under irradiation with ultraviolet light emitted from a high-pressure mercury lamp to find immediate start of the reaction which was completed after 10 hours. Distillation of the reaction mixture thus obtained gave the desired cyclohexyl methyl dichlorosilane in a yield of 85%.

EXAMPLE 4

Into the same reaction vessel as used in Example 1 was introduced 1.0 mole of cyclopentene admixed with 0.50 g of the same platinum catalyst as used in Example 1 and the mixture in the vessel was heated at 40° C. Thereafter, 1.0 mole of trichlorosilane was added dropwise to the mixture in the reaction vessel under irradiation with ultraviolet light emitted from a high-pressure mercury lamp. The reaction was completed after 6 hours. Distillation of the thus obtained reaction mixture gave the desired cyclopentyl trichlorosilane in a yield of 93%.

EXAMPLE 5

Into the same reaction vessel as used in Example 1 was introduced 1.0 mole of cyclooctene admixed with 0.22 g of the same platinum catalyst as used in Example 1 and the mixture was heated at 70° C. Thereafter, 1.0 mole of methyl dichlorosilane was added dropwise to the mixture in the reaction vessel under irradiation with ultraviolet light emitted from a high-pressure mercury lamp. The reaction was completed within 10 hours. Distillation of the thus obtained reaction mixture gave the desired cyclooctyl methyl dichlorosilane in a yield of 90%.

EXAMPLE 6

Into the same reaction vessel as used in Example 1 was introduced 1.0 mole of norbornylene with admixture of 0.06 g of solution of chloroplatinic acid in 2-ethylhexyl alcohol containing 20% by weight of $H_2PtCl_6.6H_2O$ or 7.5% by weight of Pt and the mixture was heated at 70° C. Thereafter, 1.0 mole of methyl dichlorosilane was added dropwise into the mixture in the reaction vessel under irradiation with ultraviolet light emitted from a low-pressure mercury lamp (model LP-11B, manufactured by Toshiba Co.). The reaction was completed within 6 hours. Distillation of the thus obtained reaction mixture gave the desired norbornyl methyl dichlorosilane in a yield of 91%.

EXAMPLE 7

Into the same reaction vessel as used in Example 1 was introduced 1.0 mole of 5-perfluorohexyl norbornylene admixed with 0.06 g of the same solution of platinum catalyst as used in Example 6 and the mixture was heated at 70° C. Thereafter, 1.0 mole of methyl dichlorosilane was added dropwise to the mixture in the reaction vessel under irradiation with ultraviolet light emitted from a high-pressure mercury lamp. The reaction was completed within 6 hours. Distillation of the thus obtained reaction mixture gave the desired 5-perfluorohexylnorbornyl methyl dichlorosilane in a yield of 90%.

EXAMPLE 8

Into the same reaction vessel as used in Example 1 was introduced 1.0 mole of cyclohexene admixed with 0.23 g of the same platinum catalyst as used in Example 1 and the mixture was heated at 70° C. Thereafter, 1.0 mole of trimethoxy silane was added dropwise into the mixture in the reaction vessel under irradiation with ultraviolet light emitted from a high-pressure mercury lamp. The reaction was completed within 7 hours. Distillation of the thus obtained reaction mixture gave the desired cyclohexyl trimethoxy silane in a yield of 91%.

EXAMPLE 9

Into a glass-made flask of 100 ml capacity equipped with a reflux condenser and stirrer were introduced 0.25 mole of cyclohexene, 0.25 mole of methyl dichlorosilane and 0.11 g of the same platinum catalyst as used in Example 1 and the flask containing the mixture was put under direct sun light at room temperature. A reaction took place in the mixture and continued without loss of the catalyst activity. The reaction was almost complete after 70 hours of exposure to sun light. Distillation of the thus obtained reaction mixture gave cyclohexyl methyl dichlorosilane in a yield of 91%.

What is claimed is:

1. A method for the preparation of a cycloalkyl silane compound which comprises:
   (A) admixing an unsaturated cyclic hydrocarbon compound represented by the general formula $C_m R^1{}_n A_p$, in which $R^1$ is a hydrogen atom, a fluorine atom or a fluorine-substituted or unsubstituted monovalent hydrocarbon group having 1 to 8 carbon atoms, A is a divalent intramolecular bridging group selected from methylene group $>CH_2$ and dimethylmethylene group $>C(CH_3)_2$, m is an integer of 4 to 8, p is zero or 1 and n is an integer given by $n=2m-2p-2$, with a hydrogen silane compound represented by the general formula $HR^2_qSiX_{3-q}$, in which $R^2$ is an unsubstituted or substituted monovalent hydrocarbon group, X is a halogen atom or an alkoxy group and q is zero, 1 or 2, and a platinum catalyst prepared by heating chloroplatinic acid in an alcohol, to form a reaction mixture; and (B) irradiating the reaction mixture with light to effect the hydrosilylation reaction between the unsaturated cyclic hydrocarbon compound and the hydrogen silane compound.

2. The method for the preparation of a cycloalkyll silane compound as claimed in claim 1 wherein the light is ultraviolet light.

3. The method for the preparation of a cycloalkyl silane compound as claimed in claim 1 wherein the amount of the platinum catalyst is at least 20 ppm by weight calculated as platinum based on the amount of the hydrogen silane compound.

4. The method as claimed in claim 1 wherein the alcohol is 2-ethylhexyl alcohol.

5. The method as claimed in claim 4 wherein the light is ultraviolet light and wherein the amount of the platinum catalyst is at least 20 ppm by weight calculated as platinum based on the amount of the hydrogen silane compound.

6. A method for the preparation of a cyclohexyl silane compound which comprises:
(A) admixing cyclohexene with a hydrogen silane compound represented by the general formula $HR^2_qSiX_{3-q}$, in which $R^2$ is an unsubstituted or substituted monovalent hydrocarbon group, X is a halogen atom or an alkoxy group and q is zero, 1 or 2, and a platinum catalyst prepared by heating chloroplatinic acid in an alcohol to form a reaction mixture; and (B) irradiating the reaction mixture with light to effect the hydrosilylation reaction between cyclohexene and the hydrogen silane compound.

7. The method for the preparation of a cycloalkyl silane compound as claimed in claim 6 wherein the light is ultraviolet light.

8. The method as claimed in claim 6 wherein the alcohol is 2-ethylhexyl alcohol.

9. The method as claimed in claim 8 wherein the light is ultraviolet light and wherein the amount of the platinum catalyst is at least 20 ppm by weight calculated as platinum based on the amount of the hydrogen silane compound.

* * * * *